United States Patent [19]

Idris

[11] Patent Number: 4,869,271
[45] Date of Patent: Sep. 26, 1989

[54] BI-LATERAL SURGICAL DRAPE

[75] Inventor: Carletta-Grier Idris, Acworth, Ga.

[73] Assignee: Kimberly-Clark Corporation, Neenah, Wis.

[21] Appl. No.: 285,471

[22] Filed: Dec. 16, 1988

[51] Int. Cl.$^4$ .............................................. A61F 13/00
[52] U.S. Cl. .................................... 128/853; 128/849; 128/854; 604/356
[58] Field of Search .............. 128/849, 850, 851, 852, 128/853, 854, 855; 604/356, 357

[56] References Cited

U.S. PATENT DOCUMENTS

| | | | |
|---|---|---|---|
| 3,347,544 | 10/1967 | Uffenorde | 269/328 |
| 3,791,382 | 2/1974 | Collins | 128/132 D |
| 4,089,331 | 5/1978 | Hartigan et al. | 128/850 |
| 4,169,472 | 10/1979 | Morris | 128/132 D |
| 4,378,794 | 4/1983 | Collins | 128/853 |
| 4,489,720 | 12/1984 | Morris et al. | 128/853 |
| 4,559,937 | 12/1985 | Vinson | 604/356 |
| 4,570,628 | 2/1986 | Neal | 128/853 |
| 4,589,408 | 5/1986 | Singer | 128/132 R |
| 4,596,245 | 6/1986 | Morris | 128/852 |
| 4,598,458 | 7/1986 | McAllester | 128/853 |

OTHER PUBLICATIONS

3M Brochure entitled "A Complete Ophthalmic Draping System", (partial).
Mars White Knight Company—"Supplementary and Major Drape Sheets"—Jan. 1, 1988–p. 12.
"Convertors Product Guide"—p. 18.
Medical Concepts Development—"Specialty Product Guide"–Mar. 1, 1988–pp. 1–11.
Johnson & Johnson/Surgikos—"Barrier Ophthalmology Sheet (Apertured) with Fabric 450, Reorder 1213".

Primary Examiner—Robert A. Hafer
Assistant Examiner—Lynda M. Cofsky
Attorney, Agent, or Firm—Patrick C. Wilson

[57] ABSTRACT

A fenestrated surgical drape is disclosed which has a fluid collection pouch pivotally attached about the fenestration so that the pouch may selectively attached to either side of the fenestration. As a result, the same surgical drape may be used for either right- or left-handed procedures.

10 Claims, 2 Drawing Sheets

BI-LATERAL SURGICAL DRAPE

BACKGROUND OF THE INVENTION

The present invention relates to a new and improved surgical drape with a fluid collection system. More specifically, the drape of the present invention is fenestrated and has a reversibly-attachable fluid collection pouch which may be selectively secured to either side of the fenestration. The reversibility of the pouch allows the surgical team to adapt the drape for use on either side of the fenestration.

Surgical drapes with fenestrations are well known in the art. Many such drapes are often used in surgical procedures where fairly large amounts of body fluids or irrigation liquids are emitted from the fenestrated operating site. Numerous means have been developed to absorb, retain and/or collect such fluids. Early surgical procedures often involved the use of absorbent towels to square off the operating site. These towels would in turn act to absorb fluids. Gradually, the designs were improved to include absorbent materials built into the drape itself, including such materials as foam located about the fenestration. When large amounts of fluid were being used or emitted from the incision area, bags and other types of drainage apparatus were employed to channel, collect or drain the fluids away from the operating site. Examples of such systems can be found in neurological, obstetrical (c-section) and orthopedic (arthroscopy) drapes.

Many of today's surgical drapes are customized to be compatible with specific procedures such as neurological, obstetric, orthopedic, cardiovascular and opthamic procedures. Several procedures such as eye, abdominal, limb and back surgery may be performed on either the right- or the left-hand side of the body, depending upon the ailment or injury. As a result, many of these customized drapes must be stocked in either right-handed or left-handed models to accommodate the specific procedure or else a more expansive cumbersome design must be used to cover all options. It is therefore an object of the present invention to provide a surgical drape design which will reduce the need for such duplicate stock.

Another reason for the need to inventory both left- and right-handed stock is the fact that certain operating room designs, as well as the preferences of certain surgeons, dictate that a procedure be performed from either the left or the right side of the patient. Consequently, there is a further need for surgical drape designs which are more universal in their application.

Certain surgical drapes, such as Collins (U.S. Pat. No. 3,791,382), disclose surgical drapes for abdominal surgery with pouches on either side of the incision area. Typically, however, to the extent possible fluid will be directed to the pouch on the side of the table opposite the surgeon. This is because during the procedure the surgeon will oftentimes lean up against the side of the operating table in which case contact with the fluid-filled pouch on the surgeon's side of the table may cause the pouch to collapse, thereby causing the fluid to run out over the surgeon and the operating floor. This provides potentially hazardous situations due to slipping, electrical shock and infection. Conversely, certain ophthalmic drapes, such as the Surgikos Phaco extracapular pack #1226 by the Johnson and Johnson Company, provide a fluid collection pouch in the surgical pack which is initially detached from the surgical drape. Once the drape is in place, the pouch is attached to the drape in close proximity to the fenestration on either the right- or left-hand side of the drape. Having the pouch initially detached from the drape is not a desirable feature to some operating room personnel as it increases the number of items which must be accounted for at the end of the surgical procedure. The present invention is an improvement over the above-discussed surgical drape design, in that it provides an attached fluid collection pouch which may be selectively pivoted and adhered to either side of the fenestration. This feature also provides improved turn around time in high volume procedures such as opthalmic surgeries. A further understanding of the present invention may be gained from a more detailed review of the following specification, drawings and claims.

SUMMARY OF THE INVENTION

The present invention relates to a bi-lateral surgical drape which is fenestrated. Attached about the fenestration is a fluid collection pouch which may be pivoted and selectively secured to either side of the fenestration. The reversibility of the pouch allows the surgical team to adapt the drape for use on either the left- or right-hand side of the fenestration. To secure the pouch to the drape, the drape is also supplied with double-sided adhesive tape. In addition, to further control fluid run-off from the fenestration, the surgical drape may also include a fluid trough extending at least partially or preferably entirely around the fenestration. During use, the open side of the fluid trough creates a channel about the exterior of the fenestration to collect any stray fluid run-off.

DESCRIPTION OF THE PREFERRED EMBODIMENTS

The surgical drape will now be described in in conjunction with its design and use in ophthalmic surgery. In particular, as will be described below, the novel features of the present invention will allow the operating team to use one drape and elect whether to use the fluid collection pouch on either side of the fenestration depending upon the needs of the procedure. It should be understood, however, that the description of the present invention in conjunction with its use in an ophthalmic drape is for illustration purposes only. Drapes designed for other surgical procedures which embody the present invention are also considered to be within the scope of the appended claims.

Figure 1:
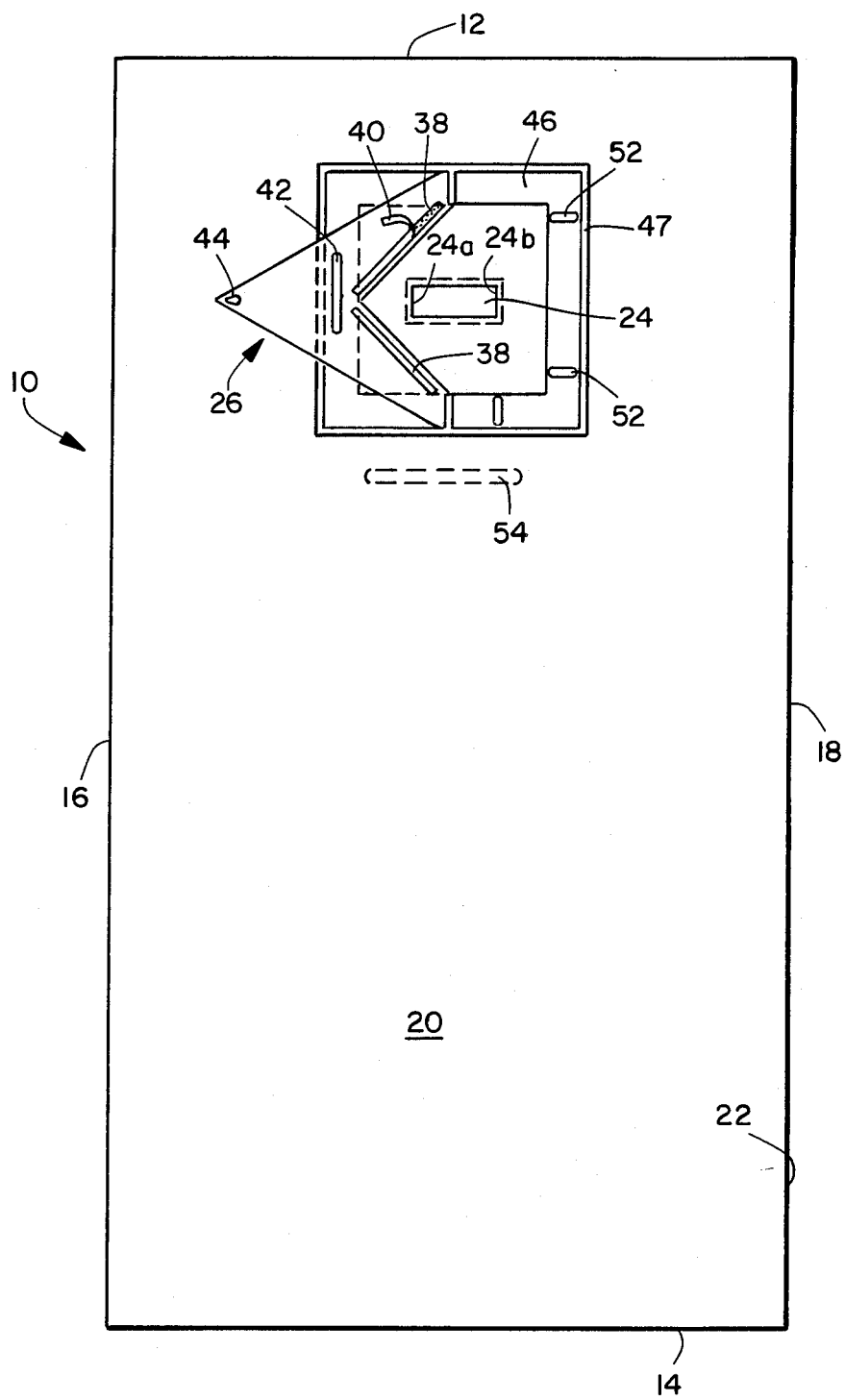
FIG. 1 is a top plan view of the bi-lateral surgical drape of the present invention.

Referring now to FIG. 1, there is shown a drape or mainsheet 10 including a top edge 12 and a bottom edge 14 joined by a pair of opposed side edges 16 and 18 thereby defining a top surface 20 and a bottom surface 22 with a fenestration 24 located interiorly therein. In a drape design such as an ophthalmic drape the dimensions should generally be from about 70 to 140 inches long with a width of from about 50 to 70 inches. Most typically, the fenestration 24 having opposed sides 24a and 24b is centrally located from the side edges 16 and 18. In addition, the fenestration 24 is located approximately 30 inches from the top edge 12 so there is sufficient material on the drape 10 to extend down over the head of the patient in one direction and as far as the patient's knees or lower in the other direction.

The drape 10 may be made from any number of materials such as cloth, nonwovens (spunbonds, meltblowns, bonded carded webs, etc.), plastic films or a combination of the foregoing. In preferred embodiments, the drape 10 is fluid-impervious at least about the fenestration site 24 to prevent fluid strike-through. It is particularly important that ophthalmic drapes be fluid-impervious since certain procedures are performed while the patient is awake. It is also preferred that the material, in addition to being fluid-impervious, be breathable to enhance patient comfort. One such material which provides these attributes is a spunbond/meltblown/spunbond laminate manufactured by the assignee of record, Kimberly-Clark Corporation, and sold under the trademark "EVOLUTION".

Figure 2:
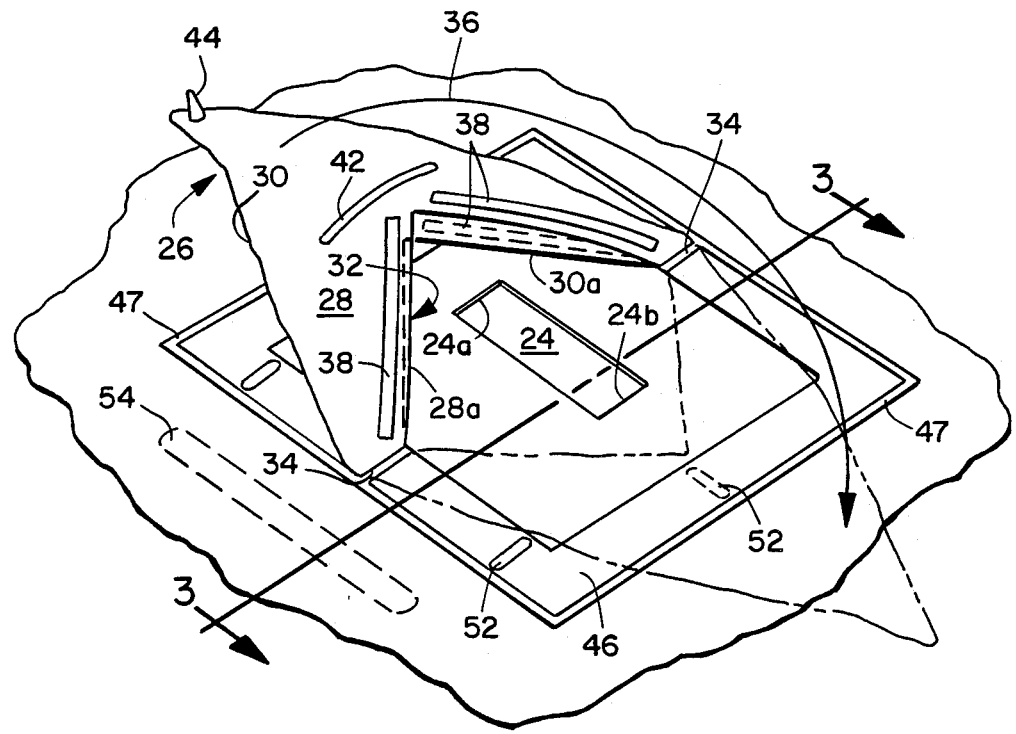
FIG. 2 is an enlarged view of the fluid control pouch of the drape shown in FIG. 1 according to the present invention.

Pivotally attached about its opening to the top surface 20 of the drape 10 is a fluid collection pouch 26. Referring to FIG. 2, the fluid collection pouch 26 is formed from a first sheet 28 and a second sheet 30 having commonly joined side edges with open top edges (28a, 30a) thereby defining a fluid receiving chamber 32. Each of the top edges 28a and 30a are cut out inwardly toward the bottom of the pouch 26 such that they will not overlap the fenestration 24. The junctures of the top (28a, 30a) and side edges are permanently secured to the top surface 20 of the drape 10 be securing means 34 such as adhesive tape, hot melt adhesive or heat sealed joints, for example. Attachment of the pouch 26 to the drape 10 should be in such a fashion that the pouch can be selectively pivoted about the secured area to either side of the fenestration 24 as shown by the arrow 36 in FIGS. 2. In either position, it can be seen that the open top edges 28a, 30a of the pouch 26 do not interfere with or overlap the fenestration 24.

To secure the pouch to the drape 10, both the first and second sheets 28 and 30 of the pouch 26 are provided with fastening means 38 directly adjacent their top edges 28a and 30a. Most preferably the fastening means 38 are double-sided adhesive tapes with release paper 40 on the sides opposite those affixed to the pouch 26. Thus, if the pouch 26 is to be affixed to the right side of the fenestration 24, the fastening means 38 is used to secure the first sheet 28 to the right side of the fenestration 24. Conversely, if the pouch is to b affixed to the left side of the fenestration 24, the fastening means 38 located on the second sheet 30 is used to secure the second sheet 30 to the left side of the fenestration 24. Alternatively, the fastening means 38 may be initially attached to the drape 10 instead of the pouch 26 and used to secure the pouch 26 to either side of the fenestration 24. As a result, the drape 10 may be used to selectively channel and collect fluids from either side of the drape 10 by simply pivoting and adhering the pouch 26 to the proper side of the drape 10.

To keep the pouch open to receive fluids, the first and second sheets 28 and 30 may be fitted with malleable strips 42. adjacent the respective top edges 28a and 30a which may be hand-formed to keep the pouch 26 open to properly receive fluids. The malleable strips 42 may be made from soft metal with or without plastic coating and secured to the inside or outside of first and second sheets 28 and 30.

The fluid collection pouch 26 also may be fitted with a drain fitting 44 adjacent the lowermost position of the fluid receiving chamber 32 to allow for the drainage of collected fluids from the pouch 26. Most typically the drain fitting 44 is connected to flexible tubing (not shown) which is fed into a fluid receptacle such as a bucket (not shown) to collect the drained fluids.

Figure 3:
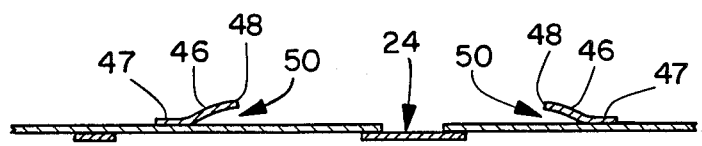
FIG. 3 is a cross-sectional view of the fluid control system taken along line 2—2 of FIG. 2.

To further control fluid run-off from the fenestration 24, the surgical drape 10 may also include a fluid trough 46 extending at least partially or preferably entirely around the fenestration 24 as shown in FIGS. 1 and 2 and in cross-section in FIG. 3. The outer most edge 47 of the trough 46 may be secured to the top 20 of the surgical drape 10 by such means as heat sealing or adhesive so as to form a fluid tight seal about its periphery. In addition, the material for the fluid trough 46 should be fluid impermeable so as to contain fluids. During use, the open side 48 of the fluid trough 46 creates a channel 50 about the exterior of the fenestration. To help keep the channel 50 open, the fluid trough 46 may be fitted with malleable opening strips 52 similar to those described in conjunction with reference numeral 42 to keep the fluid trough in an open position.

Lastly, the drape or mainsheet 10 may also be fitted with malleable strips 54 similar to those discussed above. Most preferably such strips 54 would be fitted to the mainsheet 10 in the area overlying the nose and mouth region of the patient to lift the mainsheet off the patient's face to facilitate breathing.

Having thus described the invention in detail, it should be appreciated by those skilled in the art that various modifications may be made in the present invention without departing from the scope and spirit of the following claims.

We claim:

1. A surgical drape comprising:
    a mainsheet including a top edge and a bottom edge joined by a pair of opposed side edges, thereby defining a top surface and a bottom surface, with a fenestration located therein, said fenestration having opposed sides, and
    a fluid collection pouch formed from a first sheet and a second sheet having commonly joined side edges and unattached top edges, thereby defining a fluid receiving chamber therein, and releasably fastenable fastening means located on said first and second sheets of said fluid collection pouch adjacent said unattached top edges, said fluid collection pouch being pivotally attached to said drape generally centrally of and on opposed sides of said fenestration with said unattached top edges straddling said fenestration whereby said pouch may be selectively pivoted and secured to said drape on either of said opposed sides of said fenestration using said fastening means thereby trapping and collecting fluid run-off from said fenestration.

2. The surgical drape of claim 1 wherein said fluid collection pouch contains malleable opening strips attached to said fluid collection pouch adjacent said unattached top edges for keeping said top edges in an open position.

3. The surgical drape of claim 2 wherein said fluid collection pouch is fitted with a drain fitting.

4. The surgical drape of claim 1 wherein said fluid collection pouch is fitted with a drain fitting.

5. The surgical drape of claim 1 wherein said top surface of said drape has secured thereto a fluid trough which at least partially surrounds said fenestration for trapping fluids.

6. A surgical drape comprising:
a mainsheet including a top edge and a bottom edge joined by a pair of opposed side edges, thereby defining a top surface and a bottom surface, with a fenestration located therein, said fenestration having opposed sides, and
a fluid collection pouch formed from a sheet and a second sheet having commonly joined side edges and unattached top edges, thereby defining a fluid receiving chamber therein, and releasably fastenable fastening means attached to said top surface of said mainsheet on opposed sides of said fenestration, said fluid collection pouch being pivotally attached to said drape generally centrally of and on opposed sides of said fenestration with said unattached top edges straddling said fenestration whereby said pouch may be selectively pivoted and secured to said drape on either of said opposed sides of said fenestration using said fastening means thereby trapping and collecting fluid run-off from said fenestration.

7. The surgical drape of claim 6 wherein said fluid collection pouch contains malleable opening strips attached to said fluid collection pouch adjacent said unattached top edges for keeping said top edges in an open position.

8. The surgical drape of claim 7 wherein said fluid collection pouch is fitted with a drain fitting.

9. The surgical drape of claim 6 wherein said fluid collection pouch is fitted with a drain fitting.

10. The surgical drape of claim 6 wherein said top surface of said drape has secured thereto a fluid trough which at least partially surrounds said fenestration for trapping fluids.

* * * * *

UNITED STATES PATENT AND TRADEMARK OFFICE
CERTIFICATE OF CORRECTION

PATENT NO.  : 4,869,271

DATED       : September 26, 1989

INVENTOR(S) : Carletta Grier-Idris

It is certified that error appears in the above-identified patent and that said Letters Patent is hereby corrected as shown below:

On the title page, the inventor "Carletta-Grier Idris" should read --Carletta Grier-Idris--;

Column 1, line 33, "opthamic" should read --ophthalmic--;

Column 2, line 12, "opthalmic" should read --ophthalmic--;

Column 2, line 46, "in in" should read --in--;

Column 3, line 38, "Figures" should read --Figure--;

Column 3, line 50, "is to b" should read -- is to be--;

Column 3, line 63, "42. adjacent" should read --42 adjacent--;

Column 5, line 9, "from a sheet" should read --from a first sheet--.

Signed and Sealed this

Sixteenth Day of March, 1993

Attest:

STEPHEN G. KUNIN

*Attesting Officer*     Acting Commissioner of Patents and Trademarks